(12) United States Patent
Brennan et al.

(10) Patent No.: US 8,674,169 B2
(45) Date of Patent: Mar. 18, 2014

(54) ABSORBENT CORE

(75) Inventors: Jonathan Paul Brennan, Sharonville, OH (US); Giovanni Carlucci, Chieti (IT); Maurizio Tamburro, Sambuceto (IT)

(73) Assignee: The Procter and Gamble Company, Cincinnati, OH (US)

( * ) Notice: Subject to any disclaimer, the term of this patent is extended or adjusted under 35 U.S.C. 154(b) by 249 days.

(21) Appl. No.: 13/183,482

(22) Filed: Jul. 15, 2011

(65) Prior Publication Data

US 2012/0016326 A1 Jan. 19, 2012

Related U.S. Application Data

(60) Provisional application No. 61/364,450, filed on Jul. 15, 2010.

(51) Int. Cl.
*A61F 13/15* (2006.01)

(52) U.S. Cl.
USPC ........... 604/367; 604/358; 604/370; 604/372; 604/374

(58) Field of Classification Search
USPC ......... 604/358, 364, 378, 379, 380, 367, 370, 604/372, 374, 384
See application file for complete search history.

(56) References Cited

U.S. PATENT DOCUMENTS

| | | | |
|---|---|---|---|
| 5,284,703 A | 2/1994 | Everhart et al. | |
| 7,744,576 B2 | 6/2010 | Busam et al. | |
| 7,750,203 B2 | 7/2010 | Becker et al. | |
| 7,851,667 B2 | 12/2010 | Becker et al. | |
| 2004/0162536 A1 | 8/2004 | Becker et al. | |
| 2004/0167486 A1 | 8/2004 | Busam et al. | |
| 2007/0156108 A1 | 7/2007 | Becker et al. | |
| 2007/0167928 A1 | 7/2007 | Becker et al. | |
| 2007/0179464 A1 | 8/2007 | Becker et al. | |
| 2007/0228064 A1 | 10/2007 | Brennan et al. | |
| 2008/0125735 A1 | 5/2008 | Busam et al. | |
| 2009/0043273 A1 | 2/2009 | Carlucci et al. | |
| 2009/0110998 A1 | 4/2009 | Miyachi et al. | |
| 2009/0287174 A1 | 11/2009 | Carlucci et al. | |
| 2010/0036342 A1 | 2/2010 | Carlucci et al. | |
| 2010/0048072 A1 | 2/2010 | Kauschke et al. | |
| 2010/0228210 A1 | 9/2010 | Busam et al. | |
| 2010/0228211 A1 | 9/2010 | Becker et al. | |
| 2010/0239946 A1 | 9/2010 | Miyachi et al. | |
| 2010/0262104 A1 | 10/2010 | Carlucci et al. | |

FOREIGN PATENT DOCUMENTS

| | | |
|---|---|---|
| EP | 1 961 850 A1 | 8/2008 |
| EP | 1961850 A1 | 8/2008 |
| EP | 2238956 A1 | 10/2010 |
| WO | WO/2007/120629 | * 10/2007 |

OTHER PUBLICATIONS

International Search Report, mailed Nov. 7, 2011, 5 pages.
PCT Search Report, mailed Nov. 7, 2011, 12 pages.

* cited by examiner

*Primary Examiner* — Lynne Anderson
*Assistant Examiner* — Bradley Philips
(74) *Attorney, Agent, or Firm* — Andres E. Velarde; Brian M. Bolam (57) ABSTRACT

Absorbent core for disposable absorbent articles, for example for the absorption of menses or blood.

17 Claims, 3 Drawing Sheets

ABSORBENT CORE

CROSS REFERENCE TO RELATED APPLICATION

This application claims the benefit of U.S. Provisional Application No. 61/364,450, filed on Jul. 15, 2010.

FIELD OF THE INVENTION

The present invention relates to an absorbent core for absorbent articles, for example sanitary napkins and the like.

BACKGROUND OF THE INVENTION

Absorbent articles for absorption of body fluids such as menses or blood or vaginal discharges are well known in the art, and comprise for example feminine hygiene articles such as sanitary napkins, panty liners, tampons, interlabial devices, as well as wound dressings, and the like. When considering for example sanitary napkins, these articles typically comprise a liquid-pervious topsheet as a wearer-facing layer, a backsheet as a garment-facing layer and an absorbent core between the topsheet and the backsheet. The body fluids are acquired through the topsheet and subsequently stored in the absorbent core. The backsheet typically prevents the absorbed fluids from wetting the wearer's garment.

An absorbent core can typically comprise one or more fibrous absorbent materials, which in turn can comprise natural fibres, such as for example cellulose fibres, typically wood pulp fibres, synthetic fibres, or combinations thereof.

Absorbent articles can further comprise, typically in the absorbent core, superabsorbent materials, such as absorbent gelling materials (AGM), usually in finely dispersed form, e.g. typically in particulate form, in order to improve their absorption and retention characteristics. Superabsorbent materials for use in absorbent articles typically comprise water-insoluble, water-swellable, hydrogel-forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of fibrous layers comprised in the core, or rather localized in a more concentrated arrangement between fibrous layers.

Absorbent cores for absorbent articles having a thin structure can further provide an improved immobilization of absorbent gelling materials, particularly when the article is fully or partially loaded with liquid, and an increased wearing comfort. Such thinner structures provide absorbent articles combining better comfort, discreetness and adaptability, such as for example, thin absorbent structures where the absorbent gelling material is located and somehow kept in selected, e.g. patterned regions of the structure itself.

The present invention provides significant improvements in the above area by the incorporation of a three-layer composite substrate layer in an absorbent core structure for an absorbent article.

SUMMARY OF THE INVENTION

The present invention addresses the above needs by providing an absorbent core for an absorbent article, which comprises a substrate layer, comprising a first surface and a second surface; the absorbent core further comprises a layer of absorbent polymer material, comprising a first surface and a second surface; the absorbent core also comprises a layer of adhesive, comprising a first surface and a second surface. The layer of absorbent polymer material is comprised between the layer of adhesive and the substrate layer. The second surface of the layer of absorbent polymer material is in contact with the first surface of the substrate layer, and the first surface of the layer of absorbent polymer material is in contact with the second surface of the layer of adhesive. The substrate layer comprises a composite of at least a first layer and third layer of fibrous non-woven webs. The first layer and the third layer comprise synthetic fibers with an average fiber denier from about 1 to about 6.0. The composite further comprises a second layer comprising pulp. The first layer is joined to a face of the second layer in a face to face relationship by bonding between the layers, and the third layer is joined to a second face of the second layer in a face to face relationship by bonding between the layers. The bonding comprises intertwining of the fibers between the layers. In another embodiment the present invention relates to an absorbent core for an absorbent article, which comprises a substrate layer, comprising a first surface and a second surface; the absorbent core further comprises a layer of absorbent polymer material, comprising a first surface and a second surface; the absorbent core also comprises a layer of adhesive, comprising a first surface and a second surface; the absorbent core further comprising a cover layer, said cover layer comprising a first surface and a second surface. The layer of absorbent polymer material is comprised between the layer of adhesive and the substrate layer. The second surface of the layer of absorbent polymer material is in contact with the first surface of the substrate layer, and the first surface of the layer of absorbent polymer material is in contact with the second surface of the layer of adhesive. The layer of adhesive is comprised between the layer of absorbent polymer material and the cover layer. The second surface of the cover layer is in contact with the first surface of the layer of adhesive. The cover layer comprises a composite of at least a first layer and third layer of fibrous non-woven webs. The first layer and the third layer comprise synthetic fibers with an average fiber denier from about 1 to about 6.0. The composite further comprises a second layer comprising pulp. The first layer is joined to a face of the second layer in a face to face relationship by bonding between the layers, and the third layer is joined to a second face of the second layer in a face to face relationship by bonding between the layers. The bonding comprises intertwining of the fibers between the layers.

DETAILED DESCRIPTION OF THE INVENTION

Figure 1:
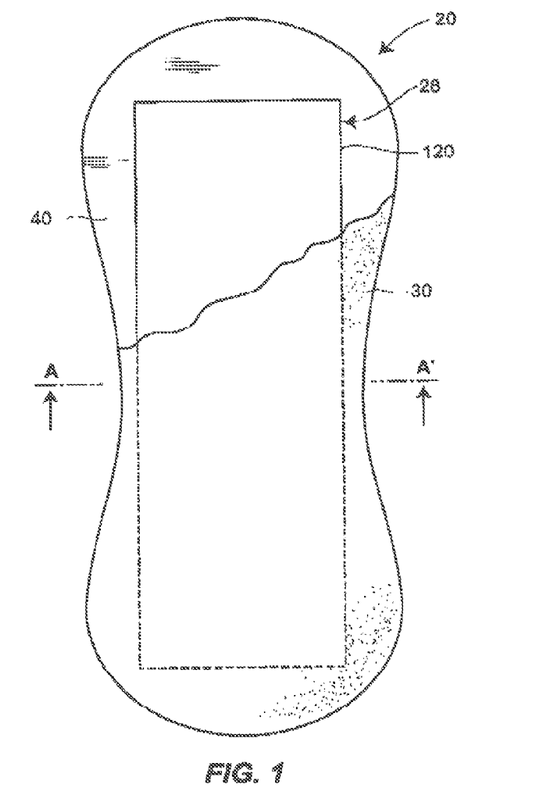
FIG. 1 is a plan view of a sanitary napkin showing an absorbent core according to an embodiment of the present invention, with portions of some constituent elements cut out in order to show underlying elements.

The present invention relates to an absorbent core for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent core according to the present invention can be for example a sanitary napkin or a panty liner. The absorbent core of the present invention will be herein described in the context of a typical absorbent article, such as, for example, a sanitary napkin 20 as illustrated in FIG. 1. Typically, such articles as shown in FIG. 1 can comprise the elements of a liquid pervious topsheet 30, a backsheet 40 and an absorbent core 28 intermediate said topsheet 30 and said backsheet 40.

In the following description of the invention, the surface of the article, or of each element thereof, which in use faces in the direction of the wearer is called wearer-facing surface. Conversely, the surface facing in use in the direction of the garment is called garment-facing surface. Therefore, the absorbent article of the present invention, as well as any element thereof, such as, for example the absorbent core, has a wearer-facing surface and a garment-facing surface.

Topsheet

According to the present invention, the absorbent article can comprise a liquid pervious topsheet. The topsheet suitable for use herein can comprise wovens, non-wovens, and/or three-dimensional webs of a liquid impermeable polymeric film comprising liquid permeable apertures. In FIG. 1 the topsheet is indicated with reference numeral 30. The topsheet for use herein can be a single layer or may have a multiplicity of layers. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. No. 3,929,135, U.S. Pat. No. 4,151,240, U.S. Pat. No. 4,319,868, U.S. Pat. No. 4,324,426, U.S. Pat. No. 4,343,314, U.S. Pat. No. 4,591,523, U.S. Pat. No. 4,609,518, U.S. Pat. No. 4,629,643, U.S. Pat. No. 4,695,422 or WO 96/00548.

Absorbent Core

Figure 2:
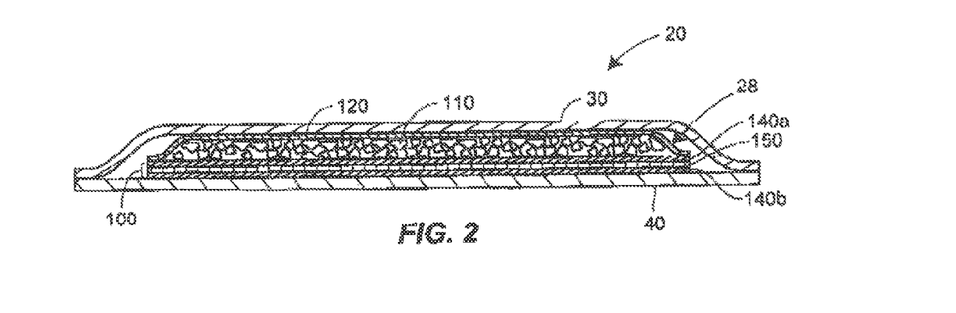
FIG. 2 is a schematic cross section of the sanitary napkin of FIG. 1 taken in the transverse axis A-A'.
Figure 3:
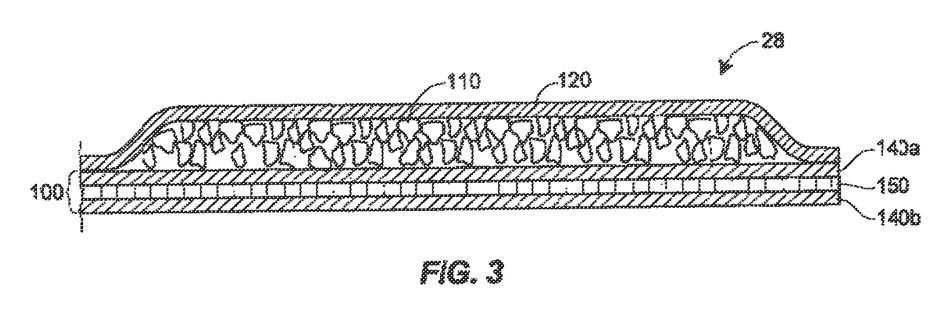
FIG. 3 shows a schematic cross section of an absorbent core according to one embodiment of the present invention.

According to an embodiment of the present invention, and as shown for example in the embodiments of FIGS. 2 and 3, the absorbent core 28 can comprise a substrate layer 100, a layer of absorbent polymer material 110 and a layer of adhesive 120. Typically the adhesive can be a hot melt adhesive. In an embodiment of the present invention, the layer of adhesive 120 can be typically for example a layer of fiberized hot melt adhesive 120. The substrate layer 100 can for example comprise a fibrous material.

Figure 4:
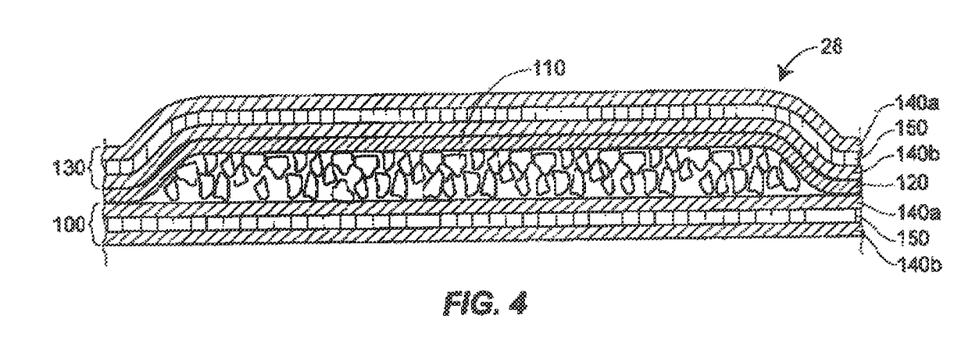
FIG. 4 shows a schematic cross section of an absorbent core according to another embodiment of the present invention.
Figure 5:
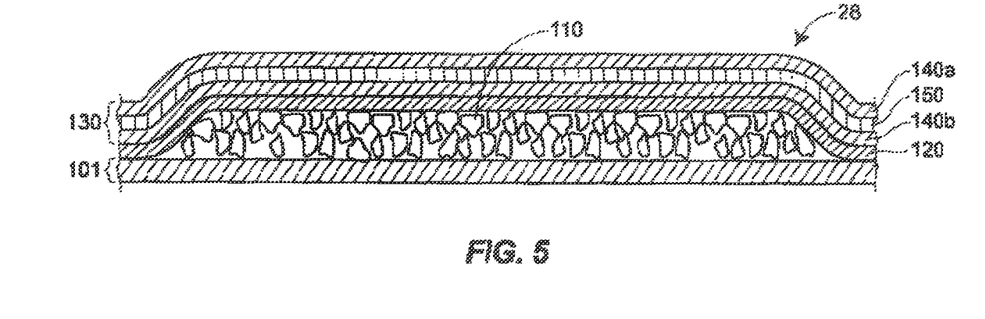
FIG. 5 shows a schematic cross section of an absorbent core according to a further embodiment of the present invention.

Alternative embodiments of the present invention are shown in FIGS. 4 and 5. The absorbent cores shown in FIGS. 4 and 5 can further comprise a cover layer 130. Suitable materials for the cover layer can be for example non-woven materials.

The substrate layer 100 of the embodiments illustrated in FIGS. 2 to 4 and the substrate layer 101 of the embodiment illustrated in FIG. 5 each comprise a first surface and a second surface. Conventionally, in all the sectional views illustrated in the attached drawings the first surface of each layer is meant to correspond to the top surface, in turn, unless stated otherwise, corresponding to the wearer facing surface of the article 20 incorporating the absorbent core, while the second surface corresponds to the bottom surface, hence in turn the garment facing surface. At least portions of the first surface of the substrate layer 100, 101 are in contact with a layer of absorbent polymer material 110. This layer of absorbent polymer material 110 comprises a first surface and a second surface, and can be typically a uniform or non-uniform layer, wherein by "uniform" or "non-uniform" it is meant that the absorbent polymer material 110 can be distributed over the substrate layer 100, 101 respectively with uniform or non-uniform basis weight over the area interested by the distribution. Conversely, the second surface of the layer of absorbent polymer material 110 is in at least partial contact with the first surface of the substrate layer 100, 101. According to an embodiment of the present invention, the layer of absorbent polymer material 110 can also be a discontinuous layer that is a layer typically comprising openings, i.e. areas substantially free of absorbent polymer material, which in certain embodiments can be typically completely surrounded by areas comprising absorbent polymer material. Typically these openings have a diameter or largest span of less than 10 mm, or less than 5 mm, or 3 mm, or 2 mm, or 1.5 mm and of more than 0.5 mm, or 1 mm. At least portions of the second surface of the absorbent polymer material layer 110 are in contact with at least portions of the first surface of the substrate layer material 100, 101. The first surface of the layer of absorbent polymer material 110 defines a certain height of the layer of absorbent polymer material above the first surface of the layer of substrate material 100, 101. When the absorbent polymer material layer 110 is provided as a non-uniform layer, typically for example as a discontinuous layer, at least some portions of the first surface of the substrate layer 100, 101 are not covered by absorbent polymer material 110. The absorbent core 28 further comprises a layer of adhesive 120, for example typically a hot melt adhesive. This typically hot melt adhesive 120 serves to at least partially immobilize the absorbent polymer material 110. According to an embodiment of the present invention, the adhesive 120 can be typically a fiberized hot melt adhesive, i.e., being provided in fibres as a fibrous layer.

In an alternative embodiment of the present invention, as illustrated in FIGS. 4 and 5, the absorbent core 28 can further comprise a cover layer 130 having respective first and second surfaces, positioned such that the second surface of the cover layer 130 is in contact with the first surface of the layer of adhesive 120, typically hot melt adhesive.

In an embodiment of the present invention comprising e.g. a non uniform layer of absorbent polymer material 110 the adhesive 120, typically hot melt adhesive, for example typically provided as a fibrous layer, can be partially in contact with the absorbent polymer material 110 and partially in contact with the substrate layer 100, 101. In such a structure, the absorbent polymer material layer 110 is provided as a discontinuous layer, a layer of adhesive 120 is laid down onto the layer of absorbent polymer material 110, typically, for example, a layer of hot melt adhesive in fiberized form, such that the second surface of the adhesive layer 120 is in direct contact with the first surface of the layer of absorbent polymer material 110, but also in direct contact with the first surface of the substrate layer 100, 101, where the substrate layer is not covered by the absorbent polymer material 110, i.e. typically in correspondence of the openings of the discontinuous layer of the absorbent polymer material 110. By saying "in direct contact," as well as more generally "in contact," as used herein, it is meant that there is no further intermediate component layer between e.g. the layer of adhesive 120 and the other respective layer in direct contact thereto, such as for example a further fibrous layer. It is however not excluded that a further adhesive material can be comprised between the layer of adhesive 120 and the optional cover layer 130, when present, or the layer of absorbent polymer material 110 or, more typically, the substrate layer 100, 101, such as for example a supplementary adhesive material provided onto the first surface of the substrate layer 100, 101 to further stabilize the overlying absorbent polymer material 110. "In direct contact" and "in contact" can hence be considered to comprise in this context a direct adhesive contact between the layer of hot melt adhesive 120 and another respective layer as explained above, or more in general direct and, typically, adhesive contact between two layers, e.g. the layer of absorbent polymer material and the substrate layer. This imparts an essentially three-dimensional structure to the fibrous layer of hot melt adhesive 120 which in itself is essentially a two-dimensional structure of relatively small thickness (in z-direction), as compared to the extension in x- and y-direction. In other words, the layer of adhesive 120 can undulate between the first surface of the absorbent polymer material 110 and the first surface of the substrate layer 100, 101. The areas where the layer of adhesive 120 is in direct contact with the substrate layer 100, when present according an embodiment of the present invention, are the areas of junction (not shown).

In the embodiments of the inventions illustrated in FIGS. 3 to 5 and in the embodiment described above, the adhesive 120 and the substrate layer 100, 101 can provide a volume to hold the absorbent polymer material 110, and can thereby immobilize this material. In a further aspect, the adhesive 120 can bond to the substrate layer 100, 101 along the perimeter of the substrate layer 100, 101, thus affixing the absorbent polymer material 110 to the substrate layer 100, 101. Typical hot melt adhesive materials can also penetrate into both the absorbent polymer material 110 and the substrate layer 100, 101, thus providing for further immobilization and affixation.

In the embodiments representatively illustrated in FIGS. 4 and 5, portions of the cover layer 130 bond to portions of the perimeter of the substrate layer 100, 101 via the adhesive 120. Thereby, the substrate layer 100, 101 together with the cover layer 130 can provide a volume to immobilize the absorbent polymer material 110.

Of course, while the typically hot melt adhesive materials disclosed herein can provide a much improved wet immobilisation, i.e. immobilisation of absorbent polymer material when the article is wet or at least partially loaded, these hot melt adhesive materials can also provide a very good immobilisation of absorbent polymer material when the article is dry.

In accordance with an embodiment of the present invention, the absorbent polymer material 110 may also be optionally mixed with fibrous material, which can provide a matrix for further immobilization of the absorbent polymer material. However, typically a relatively low amount of fibrous material can be used, for example less than about 40 weight %, less than about 20 weight %, or less than about 10 weight % of the total weight of the absorbent polymer material 110, positioned within the areas of absorbent polymer material.

According to an embodiment of the present invention, in a typically discontinuous layer of absorbent polymer material 110 the areas of absorbent polymer material can be connected to one another, while the areas of junction (not shown) can be areas, which in an embodiment may correspond to the openings in the discontinuous layer of absorbent polymer material. The areas of absorbent polymer material are then referred to as connected areas. In an alternative embodiment, the areas of junction can be connected to one another. Then, the absorbent polymer material can be deposited in a discrete pattern, or in other words the absorbent polymer material represents islands in a sea of adhesive 120. Hence, in summary, a discontinuous layer of absorbent polymer material 110 may comprise connected areas of absorbent polymer material 110 or may alternatively comprise discrete areas of absorbent polymer material 110.

The present invention, and specifically the embodiments described with reference to FIGS. 3 to 5, can be typically used to provide the absorbent core of an absorbent article, as illustrated in FIG. 1. In that case, no further materials wrapping the core, such as for example a top layer and a bottom layer are being used. With reference to the embodiments of FIGS. 4 and 5 the optional cover layer 130 may provide the function of a top layer and the substrate layer 100, 101 may provide the function of a bottom layer of an absorbent core, wherein top and bottom layers respectively correspond to the body facing and garment facing surfaces of the core 28 in an absorbent article.

According to embodiments of the present invention, the areas of direct contact between the adhesive 120 and the substrate material 100, 101 are referred to as areas of junction (not shown). The shape, number and disposition of the areas of junction will influence the immobilization of the absorbent polymer material 110. The areas of junction can be for example of squared, rectangular or circular shape. Areas of junction of circular shape can have a diameter of more than 0.5 mm, or more than 1 mm, and of less than 10 mm, or less than 5 mm, or less than 3 mm, or less than 2 mm, or less than 1.5 mm. If the areas of junction are not of circular shape, they can be of a size as to fit inside a circle of any of the diameters given above.

The areas of junction, when present, can be disposed in a regular or irregular pattern. For example, the areas of junction may be disposed along lines. These lines may be aligned with the longitudinal axis of the absorbent core, or alternatively they may have a certain angle in respect to the longitudinal edges of the core. A disposition along lines parallel with the longitudinal edges of the absorbent core 28 might create channels in the longitudinal direction which can lead to a lesser wet immobilization, hence for example the areas of junction can be arranged along lines which form an angle of about 20 degrees, or about 30 degrees, or about 40 degrees, or about 45 degrees with the longitudinal edges of the absorbent core 28. Another pattern for the areas of junction can be a pattern comprising polygons, for example pentagons and hexagons or a combination of pentagons and hexagons. Also typical can be irregular patterns of areas of junction, which also can give a good wet immobilization. Irregular patterns of areas of junction can also give a better fluid handling behaviour in case of absorption of menses or blood or vaginal discharges, since fluid can start diffusing in whichever direction from any initial acquisition point with substantially the same probability of contacting the absorbent polymer material in the e.g. discontinuous layer. Conversely, regular patterns might create preferential paths the fluid could follow with lesser probability of actually contacting the absorbent polymer material.

According to the present invention the layer of adhesive 120 can comprise any suitable adhesive material. Typically, the layer of adhesive 120 can comprise any suitable hot melt adhesive material.

Without wishing to be bound by theory it has been found that those hot melt adhesive materials can be most useful for immobilizing the absorbent polymer material 110, which combine good cohesion and good adhesion behavior. Good adhesion can typically ensure that the hot melt adhesive layer 120 maintains good contact with the absorbent polymer material 110 and in particular with the substrate material 100, 101. Good adhesion is a challenge, namely when a non-woven substrate material is present. Good cohesion ensures that the adhesive does not break, in particular in response to external forces, and namely in response to strain. The adhesive is subject to external forces when the absorbent product has acquired liquid, which is then stored in the absorbent polymer material 110 which in response swells. An exemplary adhesive should allow for such swelling, without breaking and without imparting too many compressive forces, which would restrain the absorbent polymer material 110 from swelling. It may be desirable that the adhesive does not break, which would deteriorate the wet immobilization. Exemplary suitable hot melt adhesive materials can be as described in patent application EP 1447067, particularly at sections [0050] to [0063].

The adhesive material, typically a hotmelt adhesive material, can be typically present in the form of fibres throughout the core, being provided with known means, i.e. the typically hot melt adhesive can be fiberized. Typically, the fibres can have an average thickness from about 1 µm to about 100 µm, or from about 25 µm to about 75 µm, and an average length from about 5 mm to about 50 cm. In particular the layer of typically hot melt adhesive material can be provided such as to comprise a net-like structure.

To improve the adhesiveness of the typically hot melt adhesive material 120 to the substrate layer 100, 101 or to any other layer, in particular any other non-woven layer, such layers may be pre-treated with an auxiliary adhesive.

In particular, typical parameters of a hot melt adhesive in accordance with the present invention can be as follows.

In an aspect, the loss angle tan Delta of the adhesive at 60° C. should be below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

In a further aspect, typical hot melt adhesives in accordance with the present invention may have a sufficient cohesive strength parameter γ. The cohesive strength parameter γ is measured using the Rheological Creep Test as referred to hereinafter. A sufficiently low cohesive strength parameter γ is representative of elastic adhesive which, for example, can be stretched without tearing. If a stress of τ=1000 Pa is applied, the cohesive strength parameter γ can be less than 100%, less than 90%, or less than 75%. For a stress of τ=125000 Pa, the cohesive strength parameter γ can be less than 1200%, less than 1000%, or less than 800%.

In a further aspect of the present invention, it has been found that absorbent cores can be formed by combining two of the core structures 28 shown in FIG. 3 and as described in the context thereof. The absorbent core hence can comprise two substrate layers 100, two layers of absorbent polymer material 110 and two layers of adhesive material 120. When two discontinuous layers of an absorbent polymer material 110 are used, they could be arranged in such a way that the absorbent polymer material of the one layer faces the areas of junction (not shown) of the other layer. In an alternative embodiment, however, the areas of junction can be offset and do not face each other. Typically, when two core structures are joined, this can be typically done such that the first surface of the substrate layer 100 of the first core structure faces the first surface of the substrate layer 100 of the second core structure.

According to the present invention, the absorbent polymer material 110 for the absorbent core 28 can be selected among polyacrylate based materials, typically in particle form, as described in U.S. Patent Application No. 2008/0172017 A1, herein incorporated by reference. The polyacrylate based materials incorporated in the absorbent articles of the present invention are polyelectrolytes with a multiplicity of anionic functional groups, typically carboxyl groups. In certain embodiments, the polyacrylate based materials can comprise polyacrylates, polymethacrylates, and derivatives thereof, such as for example polyacrylate sodium, polymethacrylate sodium, polyacrylate potassium, polymethacrylate potassium, starch grafted polyacrylate, starch grafted polymethacrylate, polyvinyl alcohol grafted polyacrylate, polyvinyl alcohol grafted polymethacrylate, cellulose grafted polyacrylate, cellulose grafted polymethacrylate, and the like. In an embodiment of the present invention, the absorbent gelling material can be a crosslinked, partially neutralized polyacrylate.

The polyelectrolytes which provide the polyacrylate based materials incorporated in the absorbent articles of the present invention can be made from polymerizable, unsaturated, acid-containing monomers. Such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Polyacrylate based materials, typically partially neutralized polymers, are commonly incorporated in absorbent articles and are known as superabsorbent polymers (SAP), or superabsorbents, and are crosslinked. The polyacrylate material has neutralized, typically with sodium, carboxylate groups hanging off the main polymer chain. In contact with water, the sodium detaches and goes in solution, leaving only carboxyl ions. Being negatively charged, these ions repel one another so that the polymer unwinds and absorbs more and more water, which is instead attracted by the carboxyl ions, as further carboxyl ions become available. The hydrogen in water is trapped by the polyacrylate due to the atomic bonds associated with the polarity forces between the atoms. The cross-links, which bridge different polymer chains, lead to a three dimensional structure, which upon liquid absorption constitutes the swollen gel.

According to the present invention, the absorbent polymer material 110 which can be comprised in the absorbent core 28 can be selected among the polyacrylate based polymers described in the PCT Patent Application WO 07/047,598. As explained in the referenced application, polyacrylate based materials being very slightly crosslinked, or substantially not crosslinked at all, incorporated in absorbent articles for the absorption of proteinaceous or serous body fluids such as for example menses, blood, plasma, vaginal secretions, and also mucus or milk, but particularly menses or blood, provide an improved absorption and retention capacity for such body fluids, and an improved absorption rate as well, compared to traditional crosslinked superabsorbents.

According to the above referenced application, a measure of the degree of crosslinking of a polyacrylate based polymer can be expressed in terms of the soluble or extractable fraction of the polymer. As it is known in the art, lower molecular weight polymer chains can be solubilized, or extracted, from the polymer in certain conditions, and represent said soluble or extractable fraction of the polymer itself. Generally, the extractable fraction can be considered to be inversely proportional to the degree of crosslinking, that is, the higher the degree of crosslinking, the lower the fraction, since a greater proportion of the polymer mass is actually incorporated into the polymer network. Such polyacrylate based polymer which can be incorporated in an absorbent article for absorption of proteinaceous or serous body fluids, particularly menses, has an extractable fraction of at least about 30% by weight, between about 30% and about 80% by weight, or between about 32% and about 70% by weight, evaluated according to the Extractables test method described in the PCT Patent Application WO 07/047,598. Alternatively, said polyacrylate based materials can have a retention capacity of at least about 30 g/g, at least about 35 g/g, or at least about 40 g/g, evaluated according to the Centrifuge Retention Capacity test described in the PCT Patent Application WO 07/047, 598. The absorbent polymer material can also be selected among the polyacrylate based polymers described in the PCT Patent Application WO 07/046,052. Said polymers in fact are particularly effective in absorbing complex body fluids such as menses or blood, and upon absorption of such fluids do not generally show a marked swelling, followed by gel blocking, like traditional superabsorbents, but rather act to a certain extent as thickeners of the body fluid, immobilizing it as a sort of gelatinous mass within the absorbent structure, for example in the interstices among the fibres, without causing substantial swelling and in turn a sensible increase of the overall thickness of the absorbent core.

The absorbent gelling materials can be typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The absorbent polymer particles of the layer of absorbent polymer material 110, can typically have a selected average particle size from about 200µ to about 600µ, or from about 300µ to about 500µ.

The average particle size of a material in particulate form, namely for example the absorbent polymer material, can be determined as it is known in the art, for example by means of dry sieve analysis. Optical methods, e.g. based on light scattering and image analysis techniques, can also be used.

Exemplary materials for the substrate layer 100 according to the embodiments of the present invention illustrated in FIGS. 2 to 4 comprise a three-layer composite of at least a first layer and third layer of fibrous non-woven webs comprising synthetic fibers with an average fiber denier from about 1 to about 6.0, and a second layer comprising pulp, wherein said first layer is joined to a face of said second layer in a face to face relationship by bonding between the layers and said third layer is joined to a second face of said second layer in a face to face relationship by bonding between the layers, wherein said bonding comprises intertwining of the fibers between the layers.

Materials suitable for the substrate layer 100 are described in U.S. Patent Application No. 2007/0228064 A1. The first layer 140a can be a spunbond non-woven web, the second layer 150 can comprise pulp and the third layer 140b can be a spunbond non-woven web. In this embodiment, the first layer 140a and third layer 140b of the substrate layer 100 are substantially the same, and form the outside layers of the substrate layer 100. However, it is recognized that the first and third layers, 140a and 140b, need not have substantially the same or identical compositions, basis weights, or other material properties.

In each layer of the composites of the present invention, a combination of fiber types, fiber shapes and average fiber deniers may be utilized to optimize the beneficial properties of each. For example, the outer layers, 140a and 140b, can comprise a certain percentage of synthetic fibers to give the web a soft, cloth-like feel; while the inner layer 150 may have a certain percentage of pulp fibers to provide for improved absorbency, liquid retention and thickness. In a further example, the outer layers, 140a and 140b, can comprise a certain percentage of shaped fibers in order to provide the substrate layer 100 with good opacity.

Other fibers of use in each layer include but are not limited to thermoplastic fibers, non-thermoplastic fibers and mixtures thereof. Non-limiting examples of non-thermoplastic fibers that may be of use include: rayon, which in turn includes but is not limited to viscose, lyocell and mixtures thereof; pulp; cotton; wool; silk; jute; linen; ramie; hemp; flax; camel hair; kenaf; and mixtures thereof. Non-limiting examples of thermoplastic fibers that may be of use include: polypropylene and copolymers of polypropylene; polyethylene and copolymers of polyethylene; polyamides and copolymers of polyamides; polyesters and copolymers of polyesters; aliphatic polyesteramides; lactic acid polymers; and lactide polymers; polyhydroxyalkanoates; and mixtures thereof. The aforementioned fibers and combinations of fibers may additionally comprise a certain percentage of each layer of the laminates as: multi-component, or conjugate fibers, such as bicomponent fibers; biconstituent fibers; non-round fibers; and combinations thereof. As noted above, each type of fiber is chosen to optimize the beneficial properties of each, such as liquid retention and softness.

In the present invention, synthetic fibers with relatively large fiber deniers make up a certain percentage of the outer layers, 140a and 140b. Synthetic fibers used have an average fiber denier from about 1.0 to about 6.0, from about 2.5 to about 6.0, from about 2.0 to about 5.0, or from 2.5 to 4.0. As used herein, the denier is a unit of measure for the linear mass density of fibers, and is defined as the mass in grams per 9000 meters. Without wishing to be bound by theory, it is believed that the use of large denier fibers provides for a substrate layer 100 with a low density and a large average pore size. It is further hypothesized without being bound thereto, that the large pores allow body fluids to be captured and trapped within the pores of the substrate layer 100.

The inner and outer layers of the substrate layer 100 may be characterized by specified percentages of the fiber types and shapes of which they are made. In some embodiments of the present invention, the substrate layer 100 may comprise from about 30% to about 70%, or from about 40% to about 60% of synthetic fibers. In addition, or in the alternative, the substrate layer 100 may comprise from about 70% to about 30%, or from about 60% to about 40% of pulp.

The fibrous non-woven webs that make up the outer layers 140a and 140b of the substrate layer 100 may be made via "spunbonding." Spunbond as used herein, refers to webs comprising "spunbond fibers." Spunbond fibers refers to small diameter fibers of polymeric material. Spunbond fibers may be formed by extruding molten thermoplastic material as filaments from a plurality of fine, usually circular capillaries of a spinneret with the diameter of the extruded filaments then being rapidly reduced as in, for example, U.S. Pat. No. 4,340, 563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. Spunbond fibers are generally not tacky when they are deposited onto a collecting surface and are generally continuous. Spunbond fibers are often about 10 microns or greater in diameter. However, fine fiber spunbond webs (having an average fiber diameter less than about 10 microns) may be achieved by various methods including, but not limited to, those described in U.S. Pat. No. 6,200,669 to Marmon et al. and U.S. Pat. No. 5,759,926 to Pike et al.

The layers that make up the substrate layer 100 are held together via inter-layer bonding. Inter-layer bonding may be achieved via any method known in the art that provides for intertwining of enough fibers between the layers such that the composite will not de-laminate under conditions encountered during typical usage. Non-limiting examples of such bonding processes include, but are not limited to spunlacing (hydroentanglement); hydroforming; and combinations thereof. Although a structure of separate layers permits preferential distribution of fiber types, it remains important that the constituent layers perform as a unitary web when utilized as a substrate layer 100.

According to the present invention, the substrate layer 100 can comprise a composite, which in turn comprises two outer layers, 140a and 140b, of spunbond synthetic non-woven webs and an inner layer 150 of pulp, wherein the layers are bonded together via spunlacing. Without wishing to be bound by theory, it is believed that bonding between the layers occurs as a result of the transfer of energy from the water to the composite during the spunlacing (hydroentanglement) process. The energy transfer causes the pulp fibers of the inner layer 150 to intertwine with synthetic fibers of the outer layers 140a and 140b.

Basis weights of the substrate layer 100 can typically range from about 25 g/m$^2$ to about 120 g/m$^2$, or from about 40 g/m$^2$ to about 70 g/m$^2$, or also from about 50 g/m$^2$ to about 60 g/m$^2$.

The substrate layer 100 may be made via any method known in the art. The fibrous non-woven webs may be made in a process that is in-line with the substrate layer 100 making process. Alternatively, the fibrous non-woven webs may be pre-formed in a process that is not in-line with the substrate layer 100 making process. For example, the outer fibrous non-woven web layers, 140a and 140b, and the inner pulp layer 150 may be provided as bonded roll goods.

The absorbent core of the present invention can optionally comprise a cover and said cover can be a fibrous cover or in some embodiments as shown in FIG. 4, can comprise a three-layer composite like the one constituting the substrate layer 100 as described above.

According to a further embodiment of the present invention illustrated in FIG. 5, the absorbent core of the present invention can comprise a cover layer 130 which comprises a three-layer composite like the one constituting the substrate layer 100 as described above, and a substrate layer 101.

According to the present invention, basis weights of the cover layer 130 can typically range from about 25 g/m$^2$ to about 120 g/m$^2$, or from about 40 g/m$^2$ to about 70 g/m$^2$, or also from about 50 g/m$^2$ to about 60 g/m$^2$.

The cover layer 130 may include a first layer 140a of a spunbond non-woven web, a second layer 150 comprising pulp, and a third layer 140b of a spunbond non-woven web. As was the case with the substrate layer 100, the first layer 140a and third layer 140b of the substrate layer 100 can be substantially the same, and form the outside layers of the cover layer 130. However, it is recognized that the first and third layers, 140a and 140b, need not have substantially the same or identical compositions, basis weights, or other material properties.

The substrate layer 101 can comprise non-woven materials comprising synthetic fibres, or natural fibres, or mixtures thereof, such as for example carded non-wovens, or more typically airlaid or wetlaid fibrous materials, such as for example latex or thermal bonded airlaid fibrous materials, comprising synthetic and natural fibres, such as for example cellulose fibres.

According to an embodiment of the present invention, as shown in FIG. 5, the substrate layer 101 can comprise a fibrous material comprising cellulose or cellulose derivative fibres, typically for example from about 40% to about 100% by weight of cellulose or cellulose derivative fibres, or from about 50% to about 95% by weight of cellulose or cellulose derivative fibres, or also from about 60% to about 90% by weight of cellulose or cellulose derivative fibres. In a core structure according to the present invention a substrate layer 101 constituted by a fibrous material comprising a substantial percentage of cellulose fibres can provide an advantage in terms of liquid distribution towards the liquid fraction which is not immediately absorbed by the upper layer of absorbent polymer material 110, and is directly acquired by the substrate layer 101.

Basis weights of the substrate layer 101 can typically range from about 10 g/m$^2$ to about 120 g/m$^2$, or from about 20 g/m$^2$ to about 100 g/m$^2$, or also from about 30 g/m$^2$ to about 70 g/m$^2$.

According to the present invention, the absorbent core can provide a more efficient fluid management, in terms of acquisition, immobilization and absorption and a better comfort, during the entire wearing time of the article, as explained above, which can be particularly useful in case of complex body fluids such as menses or blood. Overall, this increased efficiency in the composite structure according to the present invention can translate in a more effective exploitation of the absorbent capacity of the absorbent polymer material, also in presence of problematic body fluids such as menses or blood or vaginal discharges, and possibly also in a more efficient use of the entire structure of the absorbent core.

This is achieved in a structure which is typically thin and flexible, yet capable of employing more completely the absorption and immobilization capacity of the different materials, and having improved fit and resilience during absorption and therefore increased comfort during use.

According to the present invention, the absorbent core 28 can fully constitute the absorbent element in an absorbent article, or can be complemented with additional layers. Also, an absorbent article comprising an absorbent core according to the present invention can further comprise a fibrous fluid acquisition layer between the absorbent core 28 and the topsheet 30. According to an embodiment of the present invention the fluid acquisition layer can for example comprise fibrous non-woven materials made by air laying or wet laying of synthetic fibres such as polyethylene (PE), polyethylene terephthalate (PET), or polypropylene (PP).

Exemplary materials for the fluid acquisition layer could comprise spunbonded or carded non-woven materials, or airlaid materials such as for example latex bonded or thermal bonded airlaid materials. Basis weights can typically range from about 10 g/m$^2$ to about 60 g/m$^2$, or from about 25 g/m$^2$ to about 40 g/m$^2$.

According to another alternative embodiment of the present invention the absorbent article can comprise a further fibrous layer comprised between the absorbent core 28 and the backsheet 40, i.e. typically provided at the garment facing surface of the core. This optional layer can be provided by similar fibrous materials as those already described for the substrate layer 100 of the absorbent core of the present invention. This optional fibrous layer according to this further embodiment of the present invention can act as an added wicking layer receiving and distributing excess fluid which might not be fully retained by the absorbent core 28. The presence of cellulose fibres can make the layer particularly effective in acquiring and diffusing the fraction of body fluids like menses or blood which is not completely absorbed by the absorbent polymer material of the absorbent core 28.

Further materials, also typically in particle form, can be comprised in the layer of absorbent polymer material 110, for example known odor control materials, or inert materials such as silica.

Backsheet

The absorbent article of FIG. 1 comprising the absorbent core according to the present invention can also comprise a backsheet 40. The backsheet 40 may be used to prevent the fluids absorbed and contained in the absorbent structure from wetting materials that contact the absorbent article such as underpants, pants, pajamas, undergarments, and shirts or jackets, thereby acting as a barrier to fluid transport. The backsheet 40 according to an embodiment of the present invention can also allow the transfer of at least water vapor, or both water vapor and air through it.

Especially when the absorbent article finds utility as a sanitary napkin or panty liner, the absorbent article can be also provided with a panty fastening means, which provides means to attach the article to an undergarment, for example a panty fastening adhesive on the garment facing surface of the backsheet 40. Wings or side flaps meant to fold around the crotch edge of an undergarment can be also provided on the side edges of the napkin.

Test Methods

Rheological Creep Test

The Rheological Creep Test mentioned hereinabove for measuring the cohesive strength parameter γ is as described in the copending patent application EP 1447067, assigned to the Procter & Gamble Company.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for an absorbent article, said core comprising a substrate layer having a basis weight from about 75 g/m² to about 120 g/m²,
said substrate layer comprising a first surface and a second surface,
said absorbent core further comprising a layer of absorbent polymer material,
said layer of absorbent polymer material comprising a first surface and a second surface,
said absorbent core further comprising a layer of adhesive, said layer of adhesive comprising a first surface and a second surface,
wherein said layer of absorbent polymer material is comprised between said layer of adhesive and said substrate layer,
said second surface of said layer of absorbent polymer material is in contact with said first surface of said substrate layer,
and said first surface of said layer of absorbent polymer material is in contact with said second surface of said layer of adhesive,
wherein said substrate layer comprises a composite of at least a first layer and third layer of fibrous non-woven webs, said first layer and said third layer comprising synthetic fibers with an average fiber denier from about 1 to about 6.0, said composite further comprises a second layer comprising pulp, wherein said first layer is joined to a face of said second layer in a face to face relationship by bonding between the layers and said third layer is joined to a second face of said second layer in a face to face relationship by bonding between the layers, wherein said bonding comprises intertwining of the fibers between the layers.

2. An absorbent core according to claim 1, said absorbent core further comprising a cover layer comprising a first surface and a second surface, wherein said second surface of said cover layer is in contact with said first surface of said layer of adhesive.

3. An absorbent core according to claim 2, wherein said cover layer comprises a composite of at least a first layer and third layer of fibrous non-woven webs, said first layer and said third layer comprising synthetic fibers with an average fiber denier from about 1 to about 6.0, said composite further comprises a second layer comprising pulp, wherein said first layer is joined to a face of said second layer in a face to face relationship by bonding between the layers and said third layer is joined to a second face of said second layer in a face to face relationship by bonding between the layers, wherein said bonding comprises intertwining of the fibers between the layers.

4. An absorbent core according to claim 1, wherein said average fiber denier is from 2.5 to 6.0.

5. An absorbent core according to claim 1, wherein said first and third layers of said composite are spunbonded.

6. An absorbent core according to claim 1, wherein said intertwining is achieved via hydroentanglement.

7. An absorbent core according to claim 1, wherein said composite of said substrate layer comprises from about 30% to about 70% by weight of synthetic fibers and from about 70% to about 30% by weight of pulp.

8. An absorbent core according to claim 3, wherein said average fiber denier of said composite of said substrate layer and said cover layer is from 2.5 to 6.0.

9. An absorbent core according to claim 3, wherein said first and third layers of said composite of said substrate layer and said cover layer are spunbonded.

10. An absorbent core according to claim 3, wherein said intertwining is achieved via hydroentanglement.

11. An absorbent article comprising a topsheet, a backsheet and an absorbent core according to claim 1 comprised therebetween.

12. An absorbent core for an absorbent article, said absorbent core comprising a substrate layer,
said substrate layer comprising a first surface and a second surface,
said absorbent core further comprising a layer of absorbent polymer material,
said layer of absorbent polymer material comprising a first surface and a second surface, said absorbent core further comprising a layer of adhesive,
said layer of adhesive comprising a first surface and a second surface,
said absorbent core further comprising a cover layer having a basis weight from about 75 g/m² to about 120 g/m², said cover layer comprising a first surface and a second surface,
wherein said layer of absorbent polymer material is comprised between said layer of adhesive and said substrate layer,
said second surface of said layer of absorbent polymer material is in contact with said first surface of said substrate layer,
and said first surface of said layer of absorbent polymer material is in contact with said second surface of said layer of adhesive, and
wherein said layer of adhesive is comprised between said layer of absorbent polymer material and said cover layer,
said first surface of said layer of absorbent polymer material is in contact with said second surface of said layer of adhesive,
and said second surface of said cover layer is in contact with said first surface of said layer of adhesive, and
wherein said cover layer comprises a composite of at least a first layer and third layer of fibrous non-woven webs, said first layer and said third layer comprising synthetic fibers with an average fiber denier from about 1 to about 6.0, said composite further comprises a second layer comprising pulp, wherein said first layer is joined to a face of said second layer in a face to face relationship by bonding between the layers and said third layer is joined to a second face of said second layer in a face to face relationship by bonding between the layers, wherein said bonding comprises intertwining of the fibers between the layers.

13. An absorbent core according to claim 12, wherein said average fiber denier is from 2.5 to 6.0.

14. An absorbent core according to claim 12, wherein said first and third layers of said composite are spunbonded.

15. An absorbent core according to claim 12, wherein said intertwining is achieved via hydroentanglement.

16. An absorbent core according to claim 12, wherein said composite of said cover layer comprises from about 30% to about 70% by weight of synthetic fibers and from about 70% to about 30% by weight of pulp.

17. An absorbent article comprising a topsheet, a backsheet and an absorbent core according to claim 12 comprised therebetween.

* * * * *